(12) United States Patent
Mehta et al.

(10) Patent No.: US 12,097,284 B2
(45) Date of Patent: *Sep. 24, 2024

(54) MYCOPHENOLATE ORAL SUSPENSION

(71) Applicant: LIQMEDS WORLDWIDE LIMITED, Middlesex (GB)

(72) Inventors: Sandip Mehta, Ahmedabad (IN); Manish Kumar Umrethia, Ahmedabad (IN); Jayanta Mandal, Ahmedabad (IN)

(73) Assignee: LIQMEDS WORLDWIDE LIMITED, Hayes (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/442,765

(22) Filed: Feb. 15, 2024

(65) Prior Publication Data

US 2024/0197625 A1 Jun. 20, 2024

Related U.S. Application Data

(63) Continuation of application No. 18/362,179, filed on Jul. 31, 2023, now Pat. No. 11,931,455, which is a continuation of application No. 17/266,122, filed as application No. PCT/IB2019/000987 on Aug. 16, 2019, now abandoned.

(30) Foreign Application Priority Data

Aug. 18, 2018 (IN) .............. 201821030976

(51) Int. Cl.
| | | |
|---|---|---|
| A61K 9/00 | (2006.01) |
| A61K 45/06 | (2006.01) |
| A61K 47/02 | (2006.01) |
| A61K 47/10 | (2017.01) |
| A61K 47/12 | (2006.01) |
| A61K 47/14 | (2017.01) |
| A61K 47/34 | (2017.01) |
| A61K 47/38 | (2006.01) |

(52) U.S. Cl.
CPC ............ *A61K 9/0053* (2013.01); *A61K 45/06* (2013.01); *A61K 47/02* (2013.01); *A61K 47/10* (2013.01); *A61K 47/12* (2013.01); *A61K 47/14* (2013.01); *A61K 47/34* (2013.01); *A61K 47/38* (2013.01)

(58) Field of Classification Search
CPC ...... A61K 9/0053; A61K 45/06; A61K 47/02; A61K 47/10; A61K 47/12; A61K 47/14; A61K 47/34; A61K 47/38
See application file for complete search history.

(56) References Cited

U.S. PATENT DOCUMENTS

| | | |
|---|---|---|
| 4,753,935 A | 6/1988 | Nelson et al. |
| 4,786,637 A | 11/1988 | Allison et al. |
| 4,788,220 A | 11/1988 | Mody et al. |
| 5,247,083 A | 9/1993 | Knox et al. |
| 5,272,137 A | 12/1993 | Blase et al. |
| 5,688,529 A | 11/1997 | Lidgate et al. |
| 7,019,133 B2 | 3/2006 | Lee et al. |
| 7,727,751 B2 | 6/2010 | Grisenti et al. |
| 2006/0235070 A1 | 10/2006 | Hayden et al. |
| 2007/0208069 A1 | 9/2007 | Krishnan et al. |
| 2008/0260837 A1 | 10/2008 | Namburi et al. |
| 2011/0166225 A1 | 7/2011 | Verma et al. |
| 2013/0005722 A1 | 1/2013 | Senapati et al. |
| 2014/0371242 A1 | 12/2014 | Wang |
| 2015/0108033 A1 | 4/2015 | Vamvakas |
| 2016/0089437 A1 | 3/2016 | Hsiao |
| 2016/0228379 A1 | 8/2016 | Kumar et al. |
| 2016/0271070 A1 | 9/2016 | Singh et al. |
| 2016/0287594 A1 | 10/2016 | Guta et al. |
| 2017/0035774 A1 | 2/2017 | Toti et al. |
| 2020/0246261 A1 | 8/2020 | Mehta et al. |
| 2023/0372238 A1 | 11/2023 | Mehta et al. |

FOREIGN PATENT DOCUMENTS

| | | |
|---|---|---|
| CN | 1919184 A | 2/2007 |
| CN | 101185623 A | 5/2008 |
| EP | 724581 B1 | 11/1998 |
| EP | 2497467 A1 | 9/2012 |
| IN | 201621039392 A | 5/2018 |
| WO | 2002/094220 A1 | 11/2002 |
| WO | 2009/082038 A2 | 7/2009 |
| WO | 2009/108828 | 9/2009 |
| WO | 2018/067401 A1 | 4/2018 |
| WO | 2018167628 A1 | 9/2018 |
| WO | 2019/038584 A1 | 2/2019 |

OTHER PUBLICATIONS

Allen Loyd V. Jr., "Zonisamide 10-mg/mL oral suspension", International Journal of Pharmaceutical Compounding, vol. 13, No. 5, Sep. 1, 2009 (Sep. 1, 2009 ): 437, XP009508754, us ISSN: 1092-4221 Retrieved from the Internet: URL:hllps://www.ijpc.com/Abstracts/Abstracl.cfm?ABS=3015 the whole document.

Ferreira Andeerson O et al., Feasibility of amlodipine besylate, chloroquine phosphate, dapsone, phenytoin, pyridoxine hydrochloride, sulfadiazine, sulfasalazine, tetracycline hydrochloride, trimethoprim and zonisamide in SyrSpend SF PH4 oral suspensions, Journal of Pharmaceutical and Biochemical Analysis, vol. 118 (Oct. 27, 2015), pp. 105-112, XP029343664, Elsevier B.V, Amsterdam, NLISSN: 0731-7085, DOI:10.1016/J.JPBA.2015.10.032: 105-106; table 1.

(Continued)

*Primary Examiner* — Robert A Wax
*Assistant Examiner* — Quanglong N Truong
(74) *Attorney, Agent, or Firm* — Merchant & Gould P.C.; Daniel R. Evans

(57) ABSTRACT

Disclosed herein are pharmaceutical compositions in the form of a suspension for oral delivery. Some embodiments provide a pharmaceutical composition in the form of a suspension for oral delivery comprising an active pharmaceutical ingredient; water; a suspending agent; a buffering agent; and one or more of a wetting agent and a binder/filler. In some embodiments, the active pharmaceutical ingredient is selected from quetiapine, sildenafil, tadalafil, cinacalcet, ticagrelor, mycophenolate, aprepitant, zonisamide, and primidone.

1 Claim, No Drawings

(56) References Cited

OTHER PUBLICATIONS

Anonymous: "SyrSpend-SF: FAQ" FAGRRON, Jun. 1, 2016 (Jun. 1, 2016), pp. 1-13, XP055668917, Rotterdam, The Netherlands Retrieved from the Internet: URL:http://fagron.eo.za/wp-contenl/uploads/20160613_SyrSpend-SF_FAQ-for-external_KK_VN_ED_EvT_JC1.pdf, [retrieved on Feb. 14, 2020] the whole document.
International Search Report for PCT/IB2019/000987 (Feb. 21, 2020).
Anaizi et al., Stability of mycophenolate mofetil in an extemporaneously compounded oral liquid, Am. J. Health Syst. Pharm. (1998) 55(9): 926-929.
Venkataramanan et al., Stability of Mycophenolate Mofetil as an Extemporaneous Suspension, Ann. Pharmacother. (1998) 32(7-8): 755-757.
Swenson et al. Stability of mycophenolate mofetil in an extemporaneously compounded sugar-free oral liquid, Am J Health Syst Pharm (1999) 56(21): 2224-2226.
Ensom et al., Stability of Mycophenolate Mofetil in a 1:1 Mixture of Ora-Sweet and Ora-Plus, CJHP (2002) 55(1): 63-65.
Reding et al. Efficacy and pharmacokinetics of tacrolimus oral suspension in pediatric liver transplant recipients. Pediatr. Transplant (2002) 6(2): 124-126.
Kennedy et al. Stability of cyclophosphamide in extemporaneous oral suspensions. Ann. Pharmacother. (2010) 44 (2):295-301.
Ora-Plus® Oral Suspending Vehicle Product Information (2010), Paddock Laboratories, Inc., 2 pages.
Ora-Sweet® Flavored Syrup Vehicle Product Information (2010) Paddock Laboratories, Inc., 2 pages.
Ora-Sweet® SF Flavored Sugar-Free Syrup Vehicle Product Information (2010), Paddock Laboratories, Inc., 2 pages.
Fahimi et al., Physical and Chemical Stability of Mycophenolate Mofetil (MMF) Suspension Prepared at the Hospital, Iran J Pharm Res. (2012) 11(1): 171-175.
Cellcept® Oral Suspension (mycophenolate mofetil for oral suspension) Prescribing Information, as of Dec. 18, 2017.
Co-pending U.S. Appl. No. 16/494,030, filed Sep. 13, 2019 entitled "Pharmaceutical Composition of Oral Suspension of Immunosuppressive Agents", Mehta, et al.
U.S. Final Office Action dated Jul. 13, 2021 cited in U.S. Appl. No. 16/494,030 (10 pages).
U.S. Office Action dated Jan. 21, 2021 cited in U.S. Appl. No. 16/494,030 (11 pages).
U.S. Final Office Action dated Feb. 10, 2022 cited in U.S. Appl. No. 16/494,030 (9 pages).
U.S. Office Action dated Sep. 7, 2022 cited in U.S. Appl. No. 16/494,030 (10 pages).
U.S. Office Action dated Mar. 31, 2023 cited in U.S. Appl. No. 16/494,030 (8 pages).
Amendment filed Sep. 29, 2023 in co-pending U.S. Appl. No. 16/494,030 (5 pages).
Sorbitan Esters (Sorbitan Fatty Acid Esters) monograph (pp. 675-678) in the Handbook of Pharmaceutical Excipients, 6th Ed. (2009), Rowe et al. (Eds.), Pharmaceutical Press, London (7 pp.).
Co-pending U.S. Appl. No. 18/422,105, filed Jan. 25, 2024 entitled "Mycophenolate Oral Suspension", Mehta, et al.
Han et al., Targeted delivery of a model immunomodulator to the lymphatic system: Comparison of alkyl ester versus triglyceride mimetic lipid prodrug strategies, Journal of Controlled Release (2014) 177: 1-10.
Han et al., Profiling the Role of Deacylation-Reacylation in the Lymphatic Transport of a Triglyceride-Mimetic Prodrug, Pharmaceutical Research (2015) 32:1830-1844.

MYCOPHENOLATE ORAL SUSPENSION

This application is a continuation of U.S. patent application Ser. No. 18/362,179, filed on Jul. 31, 2023, now U.S. Pat. No. 11,931,455, which is a continuation of U.S. patent application Ser. No. 17/266,122, filed as PCT/IB2019/000987 on Aug. 16, 2019, which claims priority to Indian Provisional Application No. IN201821030976 filed on Aug. 18, 2018, and is incorporated herein by reference.

FIELD

This disclosure relates to pharmaceutical compositions in the form of a suspension for oral delivery. Particularly, the suspensions include a suspending agent, a buffering agent and water, in addition to the active pharmaceutical ingredient.

BACKGROUND

Many active pharmaceutical ingredients are insoluble and are only available in solid dosage forms. This makes it difficult for some patients, such as pediatric or geriatric patients, to take these medications. Formulating such ingredients into a liquid form is often challenging particularly while maintaining dosage requirements, stability and other concerns.

This disclosure contemplates pharmaceutical suspensions for oral dosage of such actives.

SUMMARY

Some embodiments provide a pharmaceutical composition in the form of a suspension for oral delivery comprising an active pharmaceutical ingredient; water, a suspending agent; a buffering agent; and one or more of a wetting agent and a binder/filler.

In some embodiments, the wetting agent is selected from alcohol, glycerin, propylene glycol, polyethylene glycol, mineral oil, benzalkonium chloride, benzethonium chloride, cetylpyridinium chloride, docusate sodium, nonoxynol 9, octoxynol, poloxamer, poloxamer 124, poloxamer 188, 237, 338, 407, polyoxyl 35 castor oil, polyoxyl 40 hydrogenated castor oil, polyoxyl 10 oleyl ether, polyoxyl 20 cetylstearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol, and a combination thereof. In some embodiments, the wetting agent is glycerin.

In some embodiments, the binder/filler is selected from one or more binders or fillers selected from acacia, agar, alginic acid, carmellose sodium, dextrin, veegum or gel white, gellan gum, sodium alginate, hydroxypropyl starch, maltodextrin, modified starch, pectin, potassium alginate, polyvinyl pyrrolidone, carboxymethyl cellulose or an alkali metal salt thereof, microcrystalline cellulose, bentonite, colloidal silicon dioxide, microcrystalline cellulose/sodium carboxymethylcellulose, and any combination thereof. In some embodiments, the binder/filler is microcrystalline cellulose/ sodium carboxymethylcellulose.

Some embodiments provide a pharmaceutical composition in the form of a suspension for oral delivery comprising an active pharmaceutical ingredient; water; a suspending agent; a buffering agent; and one or more of a wetting agent and a binder/filler. In some instances, the buffering agent is present to yield a pH of about 3 to about 8. In some embodiments, the active pharmaceutical ingredient is selected from quetiapine, sildenafil, tadalafil, cinacalcet, ticagrelor, mycophenolate, aprepitant, zonisamide, and primidone.

In some embodiments, the suspending agent is selected from gelatin, crosslinked polyacrylic acid, polymethacrylic acid, polyhydroxyethyl methacrylic acid, hydroxypropyl methyl cellulose, polyethylene glycol, sodium carboxymethyl cellulose, hyaluronic acid, chitosan, polycarbophil, pectin, copolymers of dextran, polyacrylamide, acacia, copolymer of caprolactone and ethylene oxide, carbopol 934, tragacanth, eudragit, polyvinyl pyrrolidone, polyacrylate and polyacrylate copolymer resins, celluloses and cellulose derivatives for example methyl-, ethyl- and propyl celluloses, hydroxyalkyl-celluloses, hydroxyl propyl celluloses, hydroxylpropylalkyl celluloses and the like including xanthan gum, polyvinyl resins, polyethylene glycol, polyethylene oxide, sorbitol, sucrose, xylitol, dextrose, fructose, maltitol, sugar, sodium alginate, or a combination thereof.

Some embodiments further include one or more binders or fillers selected from acacia, agar, alginic acid, carmellose sodium, dextrin, veegum or gel white, gellan gum, sodium alginate, hydroxypropyl starch, maltodextrin, modified starch, pectin, potassium alginate, polyvinyl pyrrolidone, carboxymethyl cellulose or an alkali metal salt thereof, microcrystalline cellulose, bentonite, colloidal silicon dioxide, microcrystalline cellulose/sodium carboxymethylcellulose and any combination thereof.

In some embodiments, the buffering agent is acetate, amino acids, ammonium sulfate, benzoate, bicarbonate, borate, citrate, citric acid monohydrate, disodium hydrogen phosphate, glutamate, lactate, meglumine, potassium citrate, sodium acetate, sodium citrate, sodium phosphate, sulfate, tartrate, triethanolamine, TRIS, trisodium citrate dehydrate, and any combination thereof.

Some embodiments provide a pharmaceutical composition in the form of a suspension for oral delivery comprising an active pharmaceutical ingredient, having poor wettability and log P>2.5; water; a suspending agent; a buffering agent in an amount sufficient to make the composition pH about 4 to about 8; and 300-400 mg/mL wetting agent. In some embodiments, the wetting agent is selected from alcohol, glycerin, propylene glycol, polyethylene glycol, mineral oil, benzalkonium chloride, benzethonium chloride, cetylpyridinium chloride, docusate sodium, nonoxynol 9, octoxynol, poloxamer, poloxamer 124, poloxamer 188, 237, 338, 407, polyoxyl 35 castor oil, polyoxyl 40 hydrogenated castor oil, polyoxyl 10 oleyl ether, polyoxyl 20 cetylstearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol, and a combination thereof. In some embodiments, the wetting agent is glycerin. In some embodiments, the binder/filler is selected from one or more binders or fillers selected from acacia, agar, alginic acid, carmellose sodium, dextrin, veegum or gel white, gellan gum, sodium alginate, hydroxypropyl starch, maltodextrin, modified starch, pectin, potassium alginate, polyvinyl pyrrolidone, carboxymethyl cellulose or an alkali metal salt thereof, microcrystalline cellulose, bentonite, colloidal silicon dioxide, microcrystalline cellulose/sodium carboxymethylcellulose, and any combination thereof. In some embodiments, the binder/filler is microcrystalline cellulose/ sodium carboxymethylcellulose.

Some embodiments provide a pharmaceutical composition in the form of a suspension for oral delivery comprising an active pharmaceutical ingredient, having poor wettability and log P>2.5; water; a suspending agent; a buffering agent in an amount sufficient to make the composition pH about 4 to about 8; and 300-400 mg/mL wetting agent. In some embodiments, the active pharmaceutical ingredient is selected from quetiapine, sildenafil, tadalafil, and cinacalcet. Although any suitable suspending agent can be used, in some embodiments, the suspending agent is xanthan gum and HPMC, at about 2 to about 6 mg/mL and about 10 mg/mL, respectively. Although any suitable buffering agent can be used, in some embodiments, the buffering agent is citric acid monohydrate or disodium hydrogen phosphate. Some embodiments further comprise microcrystalline cellulose/sodium carboxymethylcellulose.

In some embodiments, the active pharmaceutical ingredient is selected from quetiapine, sildenafil, tadalafil, and cinacalcet; the suspending agent is about 2 to about 6 mg/mL xanthan gum and about 10 mg/mL HPMC; the buffering agent is citric acid monohydrate or disodium hydrogen phosphate.

Some embodiments provide a pharmaceutical composition in the form of a suspension for oral delivery comprising an active pharmaceutical ingredient, having moderate wettability and lot P from about 2 to about 2.5; water; a suspending agent; a buffering agent in an amount sufficient to make the composition pH about 3 to about 8; and about 100 mg/mL wetting agent.

In some embodiments, the wetting agent is selected from alcohol, glycerin, propylene glycol, polyethylene glycol, mineral oil, benzalkonium chloride, benzethonium chloride, cetylpyridinium chloride, docusate sodium, nonoxynol 9, octoxynol, poloxamer, poloxamer 124, poloxamer 188, 237, 338, 407, polyoxyl 35 castor oil, polyoxyl 40 hydrogenated castor oil, polyoxyl 10 oleyl ether, polyoxyl 20 cetylstearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol, and a combination thereof. In some embodiments, the wetting agent is glycerin.

In some embodiments, the binder/filler is selected from one or more binders or fillers selected from acacia, agar, alginic acid, carmellose sodium, dextrin, veegum or gel white, gellan gum, sodium alginate, hydroxypropyl starch, maltodextrin, modified starch, pectin, potassium alginate, polyvinyl pyrrolidone, carboxymethyl cellulose or an alkali metal salt thereof, microcrystalline cellulose, bentonite, colloidal silicon dioxide, microcrystalline cellulose/sodium carboxymethylcellulose, and any combination thereof. In some embodiments, the binder/filler is microcrystalline cellulose/sodium carboxymethylcellulose.

Some embodiments provide a pharmaceutical composition in the form of a suspension for oral delivery comprising an active pharmaceutical ingredient, having moderate wettability and log P from about 2 to about 2.5; water; a suspending agent; a buffering agent in an amount sufficient to make the composition pH about 3.5 to about 7; and about 100 mg/mL glycerin. In some embodiments, the active pharmaceutical ingredient is selected from ticagrelor, mycophenolate, and primidone. Although any suitable suspending agent can be use, in some embodiments, the suspending agent is xanthan gum at about 2 to about 3.5 mg/mL. Any suitable buffering agent can be employed, but in some embodiments, the buffering agent is citric acid monohydrate or disodium hydrogen phosphate. In some the embodiments, the suspension further comprises microcrystalline cellulose/sodium carboxymethylcellulose.

In some embodiments, the active pharmaceutical ingredient is selected from ticagrelor, mycophenolate, and primidone; the suspending agent is about 2 to about 3.5 mg/mL xanthan gum; and the buffering agent is citric acid monohydrate or disodium hydrogen phosphate.

Some embodiments provide a pharmaceutical composition in the form of a suspension for oral deliver comprising an active pharmaceutical ingredient, having good wettability and log P less than about 2; water; a suspending agent; and a buffering agent in an amount sufficient to make the composition pH about 3 to about 6. In some embodiments the active pharmaceutical ingredient is selected from zonisamide and primidone. In some embodiments, the suspending agent is xanthan gum at about 3 to about 3.5 mg/mL, although any suitable suspending agent may be used. In some embodiments, the buffering agent is citric acid monohydrate or disodium hydrogen phosphate. Some embodiments further comprise microcrystalline cellulose/sodium carboxymethylcellulose. Some embodiments, depending on the active pharmaceutical ingredient may include up to 25 mg/mL glycerin.

In some embodiments, the suspension comprises an active pharmaceutical ingredient which is selected from ticagrelor, mycophenolate, and primidone; a suspending agent which is about 2 to about 3.5 mg/mL xanthan gum; a buffering agent which is citric acid monohydrate or disodium hydrogen phosphate; 0 to 25 mg/mL glycerin; and microcrystalline cellulose/sodium carboxymethylcellulose.

Some embodiments provide a pharmaceutical composition in the form of a suspension for oral delivery comprising an active pharmaceutical ingredient: water; a suspending agent: a stabilizing amount of wetting agent; and a buffering agent in an amount sufficient to make the composition pH about 5 to about 7.

In some embodiments, the wetting agent is selected from alcohol, glycerin, propylene glycol, polyethylene glycol, mineral oil, benzalkonium chloride, benzethonium chloride, cetylpyridinium chloride, docusate sodium, nonoxynol 9, octoxynol, poloxamer, poloxamer 124, poloxamer 188, 237, 338, 407, polyoxyl 35 castor oil, polyoxyl 40 hydrogenated castor oil, polyoxyl 10 oleyl ether, polyoxyl 20 cetylstearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol, and a combination thereof. In some embodiments, the wetting agent is glycerin.

In some embodiments, the binder/filler is selected from one or more binders or fillers selected from acacia, agar, alginic acid, carmellose sodium, dextrin, veegum or gel white, gellan gum, sodium alginate, hydroxypropyl starch, maltodextrin, modified starch, pectin, potassium alginate, polyvinyl pyrrolidone, carboxymethyl cellulose or an alkali metal salt thereof, microcrystalline cellulose, bentonite, colloidal silicon dioxide, microcrystalline cellulose/sodium carboxymethylcellulose, and any combination thereof. In some embodiments, the binder/filler is microcrystalline cellulose/sodium carboxymethylcellulose.

In some embodiments, the suspending agent is selected from gelatin, crosslinked polyacrylic acid, polymethacrylic acid, polyhydroxyethyl methacrylic acid, hydroxypropyl methyl cellulose, polyethylene glycol, sodium carboxymethyl cellulose, hyaluronic acid, chitosan, polycarbophil, pectin, copolymers of dextran, polyacrylamide, acacia, copolymer of caprolactone and ethylene oxide, carbopol 934, tragacanth, eudragit, polyvinyl pyrrolidone, polyacrylate and polyacrylate copolymer resins, celluloses and cellulose derivatives for example methyl-, ethyl- and propyl celluloses; hydroxyalkyl-celluloses, hydroxyl propyl celluloses, hydroxylpropylalkyl celluloses and the like including xanthan gum, polyvinyl resins, polyethylene glycol, polyethylene oxide, sorbitol, sucrose, xylitol, dextrose, fructose, maltitol, sugar, sodium alginate, or a combination thereof.

Some embodiments provide a pharmaceutical composition in the form of a suspension for oral delivery comprising an active pharmaceutical ingredient water; a suspending agent; a stabilizing amount of glycerin; and a buffering agent in an amount sufficient to make the composition pH about 5 to about 7. In some embodiments, the suspending agent is xanthan gum at about 2 mg/mL. In some embodiments, the buffering agent is citric acid monohydrate or disodium hydrogen phosphate. In some embodiments, the suspension further comprises microcrystalline cellulose/sodium carboxymethylcellulose.

In some embodiments, the suspension comprises a suspending agent which is about 2 mg/mL xanthan gum; a buffering agent which is citric acid monohydrate or disodium hydrogen phosphate; 0 to 25 mg/ml glycerin; and microcrystalline cellulose/sodium carboxymethylcellulose.

Other embodiments will be apparent from this specification without departing from the scope and spirit of this disclosure.

DETAILED DESCRIPTION

Generally, disclosed herein are pharmaceutical compositions in the form of a suspension for oral delivery. Particularly, the suspension includes a suspending agent, a buffering agent and water, in addition to the active pharmaceutical ingredient. Additional excipients may also be used. Glycerin is used as a wetting agent depending on the wettability of the active pharmaceutical ingredient and its log P value. In some instances, glycerin is used in stabilizing amounts rendering the wettability and log P of the active pharmaceutical ingredient more or less irrelevant. The amount of wetting agent, e.g. glycerin, is generally about 300 mg/mL to about 400 mg/mL for actives with poor wettability and log P>2.5, about 100 mg/mL for actives with moderate wettability and log P between about 2 and about 2.5, and up to about 25 mg/mL for actives with good wettability. When glycerin is used in a stabilizing amount it is greater than about 500 mg/mL.

Because of their liquid character, liquid dosage forms represent an ideal dosage form for patients who have difficulty swallowing tablets or capsules. This factor is of particular importance in administration of drugs to children and aged patients. The liquid dosage forms disclosed herein are particularly useful for administering to pediatric and geriatric patients.

Suspensions possess certain advantages over other dosage forms. Some drugs are insoluble in all acceptable media and must, therefore, be administered as a tablet, capsule, or as a suspension. In addition, disagreeable tastes can be masked by a suspension of the drug or a derivative of the drug. Drugs in suspension are chemically more stable than in solution.

The suspensions described herein provide ready to use, suspension dosage forms. Various embodiments describe ready to use, liquid dosage forms in the form of oral suspensions for use with a variety of active pharmaceutical ingredients. In one of the further aspects, liquid dosage forms of the present invention are palatable, oral ready to use formulations (i.e., do not require dilution, mixing with other solvents, or further manipulation of the composition). It may be appreciated that many of the actives have been used in parenteral and solid oral medicinal products, but have not previously been used in oral liquid preparations that were stable over extended periods and that could be retrieved from the packing in a ready to use form as contemplated herein.

The suspension is room temperature stable, requires no reconstitution, and in some embodiments may not even require shaking or mixing just prior to use, which is often required with suspensions.

Suspensions of insoluble drugs may also be used externally, often as protective agents. Drugs in suspension are chemically more stable than in solution. This is particularly important with certain drugs where the pharmacist is often called on to prepare such a suspension just prior to the dispensing of the preparation.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The following terms shall have, for the purposes of this application, the respective meanings set forth below.

"Optional" or "optionally" means that the subsequently described event or circumstance may or may not occur, and that the description includes instances where the event occurs and instances where it does not.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

This application discloses a pharmaceutical composition in the form of a suspension for oral delivery comprises an active pharmaceutical ingredient: water: a suspending agent; a buffering agent: and one or more of glycerin and microcrystalline cellulose/sodium carboxymethylcellulose. Generally, the buffering agent will be present in an amount sufficient to achieve a pH of about 3 to about 8.

The Actives. For purposes of this disclosure and patent application, the active pharmaceutical ingredient will not be an anti-cancer or chemotherapeutic agent. Typically the active pharmaceutical ingredient for use in the suspension disclosed herein are insoluble and thus not well-suited for other liquid dosage forms. In some embodiments, the liquid suspensions disclosed herein do not include a chemotherapeutic active pharmaceutical agent.

Any suitable active pharmaceutical ingredient may be used. The active pharmaceutical ingredient may be selected from quetiapine, sildenafil, tadalafil, cinacalcet, ticagrelor, mycophenolate, aprepitant, zonisamide, and primidone.

Reference to the active pharmaceutical ingredient also refers to all forms of the active, including a salt thereof, an ester thereof, a free acid form thereof, a free base form thereof, a solvate thereof, a deuterated derivative thereof, a hydrate thereof, an N-oxide thereof, a clathrate thereof, a prodrug thereof, a polymorph thereof, a stereoisomer thereof, an enantiomer thereof, a diastereomer thereof, a racemate thereof, a mixture of stereoisomers thereof, and a combination thereof.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with JAK/STAT modulating compound, can include, but is not limited to, providing an JAK/STAT modulating compound into or onto the target tissue; providing an JAK/STAT modulating compound systemically to a patient by, e.g., intravenous injection whereby the therapeutic reaches the target tissue; providing an JAK/STAT modulating compound in the form of the encoding sequence thereof to the target tissue (e.g., by so-called gene-therapy techniques). "Administering" a composition may be accomplished by injection, topical administration, orally, or by either method in combination with other known techniques.

The term "subject" as used herein includes, but is not limited to, humans and non-human vertebrates such as wild, domestic, and farm animals. In certain embodiments, the subject described herein is an animal. In certain embodiments, the subject is a mammal. In certain embodiments, the subject is a human. In certain embodiments, the subject is a non-human animal. In certain embodiments, the subject is a non-human mammal. In certain embodiments, the subject is a domesticated animal, such as a dog, cat cow, pig, horse, sheep, or goat. In certain embodiments, the subject is a companion animal such as a dog or cat. In certain embodiments, the subject is a livestock animal, such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

The term "improve" is used to convey that the compounds of embodiments herein change either the appearance, form, characteristics and/or the physical attributes of the tissue to which it is being provided, applied or administered. The change in form may be demonstrated by any of the following alone or in combination: enhanced appearance of the skin; at least partial remission, such as repigmentation of existing areas of depigmentation; uniformity of skin color; increased melanin production in white patches; repigmentation of skin; and/or reduced incidence of new areas of depigmentation.

The term "inhibit" includes the administration of a compound of embodiments herein to prevent the onset of the symptoms, alleviating the symptoms, or eliminating the disease, condition or disorder.

By "pharmaceutically acceptable", it is meant the carrier, diluent or excipient must be compatible with the other ingredients of the topical formulation and not deleterious to the recipient thereof.

As used herein, the term "therapeutic" means an agent utilized to treat, combat, inhibit, ameliorate, prevent or improve an unwanted condition or disease of a patient. In part, embodiments of embodiments herein are directed to the treatment of vitiligo.

A "therapeutically effective amount" or "effective amount" of a composition is a predetem lined amount calculated to achieve the desired effect, i.e., to induce a favorable immunological response.

Quetiapine is an atypical antipsychotic used to treat schizophrenia, bipolar disorder, major depressive disorder, and for other uses.

Sildenafil is a drug belonging to the group of selective inhibitors of phosphodiesterase-V (PDE V), an enzyme that is responsible for the degradation of cyclic guanosine monophosphate (GMPc), such that the Sildenafil promotes an increase in GMPc levels, which in turn promotes the relaxation of smooth muscle tissue. Sildenafil is approved for the treatment of Pulmonary Arterial Hypertension and is also used to treat erectile dysfunction.

Tadalafil is an active ingredient of an erectile dysfunction. Tadalafil is a selective and reversible inhibitor for cGMP-specific PDE V (phosphodiesterase type V). When nitrogen oxide is locally released due to sexual arousal, the level of cGMP is increased in the corpus cavernosum due to the inhibition of PDE V by Tadalafil. When the level of cGMP is increased in this way, smooth muscle relaxation and blood inflow to the penile tissue may result, thus causing an erection. Tadalafil has also been approved by the USFDA for the treatment of pulmonary arterial hypertension to improve exercise ability.

PDE V inhibitors such as Sildenafil and/or Tadalafil may be used in methods for the treatment of at least one disease or condition selected from the group comprising of hypertension, pulmonary hypertension, arterial hypertension, pulmonary arterial hypertension, erectile dysfunction, cirrhosis, solid tumor, heart failure, cerebral vasospasm, arthritis, rheumatoid arthritis, atherosclerosis, congenital heart diseases, Parkinson's disease, neonatal encephalopathy, preeclampsia, prostate cancer, pancreatic cancer, hepatic encephalopathy, aortic stenosis, cystic fibrosis, peripheral arterial occlusive disease, sickle cell disease, priapism, age-related macular degeneration, schizophrenia, bronchopulmonary dysplasia, impotence, lymphangioma, dysmenorrhea, urinary incontinence, chronic obstructive pulmonary disease, lymphatic malformulations, duchenne muscular dystrophy, becker muscular dystrophy, pulmonary fibrosis, nontuberculous mycobacterial infection, idiopathic pulmonary fibrosis, Raynaud's phenomenon, prostatic hyperplasia, benign prostatic hyperplasia waldenstrom's macroglobulinemia and the like comprising administering to a patient, such as human, an effective dosage amount of a liquid pharmaceutical composition comprising PDE V inhibitor drug and one or more pharmaceutically acceptable excipients or additives as disclosed and described herein. In one of the further aspects, the present invention is directed to use liquid pharmaceutical compositions of the present invention for the treatment of a disease or a condition that can be treated by administration of PDE V inhibitor drugs. In one of the further aspects, the present invention is directed to use liquid pharmaceutical compositions of the present invention for the treatment of at least one disease or a condition selected from the group comprising of hypertension, pulmonary hypertension, arterial hypertension, pulmonary arterial hypertension, erectile dysfunction, cirrhosis, solid tumor, heart failure, cerebral vasospasm, arthritis, rheumatoid arthritis, atherosclerosis, congenital heart diseases, Parkinson's disease, neonatal encephalopathy, pre-eclampsia, prostate cancer, pancreatic cancer, hepatic encephalopathy, aortic stenosis, cystic fibrosis, peripheral arterial occlusive disease, sickle cell disease, priapism, age-related macular degeneration, schizophrenia, bronchopulmonary dysplasia, impotence, lymphangioma, dysmenorrhea, urinary incontinence, chronic obstructive pulmonary disease, lymphatic malformations, duchenne muscular dystrophy becker muscular dystrophy, pulmonary fibrosis, nontuberculous mycobacterial infection, idiopathic pulmonary fibrosis, Raynaud's phenomenon, prostatic hyperplasia, benign prostatic hyperplasia waldenstrom's macroglobulinemia and the like.

Cinacalcet is chemically described as N-[1-(R)-(—)-(1-naphthyl)ethyl]-3-[3-(trifluoromethyl)phenyl]-1-aminopropane. Empirical formula of Cinacalcet free base is C22H22F3N with a molecular weight of 357.4 gm/mol. It has one chiral center having an (R)-absolute configuration. The (R)-enantiomer is the more potent enantiomer and has been shown to be responsible for pharmacodynamic activity. Cinacalcet is commercially available in particular as hydrochloride salt. Cinacalcet hydrochloride is a white to off-white, crystalline solid which is soluble in methanol or 95% ethanol and slightly soluble in water. Cinacalcet is indicated for the treatment of secondary hyperparathyroidism resulting from chronic kidney disease and for the treatment of hypercalcemia in patients with either parathyroid carcinoma or hyperparathyroidism. Currently, Cinacalcet is also in Phase III clinical trials in pediatric patients with secondary hyperparathyroidism (SHPT) and chronic kidney disease (CKD) on dialysis.

Ticagrelor is an antagonist of the $P2Y_{12}$ receptor. Ticagrelor may be used as a blood thinner. Ticagrelor is also used for the prevention of thrombotic events (for example stroke or heart attack) in people with acute coronary syndrome or myocardial infarction with ST elevation.

Mycophenolate (particularly as mycophenolate mofetil an immunosuppressant useful in minimizing rejection in organ transplantation among other things. Aprepitant (5-([2R,3S)-2-((R)-1-[3,5-bis(trifluoromethyl)phenyl]ethoxy)-3-(4-fluoro-phenyl)morpholino]methyl)-1H-1,2,4-triazol-3(2H)-one) is an antiemetic compound that belongs to the class of substance P antagonists that mediate their effect by blocking the neurokinin (NK1) receptor. Aprepitant is a selective, high-affinity antagonist at human substance P NK-1 receptors and is manufactured by Merck & Co. (available under the brand name, EMEND®. It is available as capsules (40, 80 and 125 mg) or powder (150 mg) for injection or powder for oral suspension (125 mg) for the prevention and control of acute and delayed chemotherapy induced nausea and vomiting and for the prevention of postoperative nausea and vomiting. The liquid dosage form described herein using aprepitant are suitable for administration to a subject to treat or prevent a disease or condition. Preferably, the subject is a mammal. More preferably, the mammal is a human. Preferably, the disease or condition is a disease or condition that is treatable by the administration of Aprepitant, such as those associated with Substance P/NK1 receptor. In some aspects, the disease or condition is the prevention and control of acute and delayed chemotherapy induced nausea and vomiting, and for the prevention of postoperative nausea and vomiting.

Zonisamide, chemically known as 1,2-benzoxazol-3-yl-methane-sulfonamide having an empirical formula C8H8N2O3S and a molecular weight of 212.2 gm/mol. Zonisamide is a benzisoxazole derivative, originally synthesized in Japan in 1974 during exploratory research on psychiatric drugs, where it was subsequently identified as having anticonvulsant activity during screening. Zonisamide is thought to act through its blocking of voltage-dependent sodium channels, reduction of voltage dependent T-type inward calcium currents, binding to the gamma-aminobutyric acid (GABA)-benzodiazepine receptor complex, and facilitation of both dopaminergic and serotonergic neurotransmission. Zonisamide was approved in Japan in 1989 as both monotherapy and adjunctive therapy for children and adults—with generalized or partial seizures. Zonisamide was approved in 2000 in the USA as adjunctive therapy in the treatment of partial seizures in adults with epilepsy. For epilepsy, most studies have used oral zonisamide in daily doses ranging from 200 mg/day to 600 mg/day, divided in 2 daily doses, adjusted to maintain serum levels of about 15 µg/ml to about 40 µg/ml. Zonisamide is also proposed for treatment of other disease like tardive dyskinesia. It is to be sold, when combined with bupropion, under the brand name Empatic for obesity. Zonisamide has been studied for and used as a migraine preventative medication. and has also been shown to be effective in some cases of neuropathic pain. It has also been used off label by psychiatrists as a mood stabilizer to treat bipolar depression.

Primidone is an anticonvulsant of the barbiturate class. It is a structural analog of phenobarbital and related to barbiturate-derivative anticonvulsants. The active metabolites, phenobarbital, p-hydroxyphenobarbital, and phenylethylmalonamide, are also anticonvulsants. Primidone was once a mainstay anticonvulsant in the treatment of partial and generalized seizures and was the treatment of choice for secondarily generalized seizures originating in the temporal lobes.

Suspending Agents. The viscosity of the suspension may be controlled by the use of one or more suspending agents/thickening agents (or viscosity modifying agents) suitable for pharmaceutical use. These agents ensure that the individual doses removed have constant active ingredient content. The suspending agent may be selected from gelatin, crosslinked polyacrylic acid, polymethacrylic acid, polyhydroxyethyl methacrylic acid, hydroxypropyl methyl cellulose, polyethylene glycol, sodium carboxymethyl cellulose, hyaluronic acid, chitosan, polycarbophil, pectin, copolymers of dextran, polyacrylamide, acacia, copolymer of caprolactone and ethylene oxide, carbopol 934, tragacanth, eudragit, polyvinyl pyrrolidone, polyacrylate and polyacrylate copolymer resins, celluloses and cellulose derivatives for example methyl-, ethyl- and propyl celluloses; hydroxyalkyl-celluloses, hydroxyl propyl celluloses, hydroxylpropylalkyl celluloses and the like including xanthan gum, polyvinyl resins, polyethylene glycol, polyethylene oxide, sorbitol, sucrose, xylitol, dextrose, fructose, maltitol, sugar, sodium alginate, or a combination thereof.

In some embodiments, the suspending agent is present in an amount of about 2 mg/mL to about 20 mg/mL, about 2 mg/mL to about 15 mg/mL, about 2 mg/mL to about 10 mg/mL, about 2 mg/mL to about 8 mg/mL, about 2 mg/mL to about 6 mg/mL, about 4 mg/mL to about 20 mg/mL, about 4 mg/mL to about 15 mg/mL, about 4 mg/mL to about 10 mg/mL, about 4 mg/mL to about 8 mg/mL, about 6 mg/mL to about 20 mg/mL, about 6 mg/mL to about 15 mg/mL, about 8 mg/mL to about 20 mg/mL, about 8 mg/mL to about 15 mg/mL, and any value within the foregoing range.

Binder/Filler. One or more binders/fillers may be employed in the suspensions described herein. The binders or fillers may be selected from acacia, agar, alginic acid, carmellose sodium, dextrin, veegum or gel white, gellan gum, sodium alginate, hydroxypropyl starch, maltodextrin, modified starch, pectin, potassium alginate, polyvinyl pyrrolidone, carboxymethyl cellulose or an alkali metal salt thereof, microcrystalline cellulose, bentonite, colloidal silicon dioxide and any combination thereof.

In some embodiments, the binder/filler is present in an amount of 10 mg/mL to 25 mg/mL. Some embodiments provide 15 mg/mL to 20 mg/mL.

Buffering Agent. One or more buffering agents may be employed in an amount sufficient to achieve the desired pH, dependent upon the desired active pharmaceutical ingredient. Suitable buffering agents include acetate, amino acids, ammonium sulfate, benzoate, bicarbonate, borate, citrate, citric acid monohydrate, disodium hydrogen phosphate, glutamate, lactate, meglumine, potassium citrate, sodium acetate, sodium citrate, sodium phosphate, sulfate, tartrate, triethanolamine, TRIS, trisodium citrate dehydrate, and any combination thereof.

In some embodiments, the buffering agent is present m an amount sufficient to achieve the desired pH.

As noted above, actives suitable for use in the suspensions disclosed herein are grouped by their wettability and log P or where glycerin is used as a stabilizer.

For an active pharmaceutical ingredient, having poor wettability and log P>2.5, the pharmaceutical composition in the form of a suspension for oral delivery comprises water; a suspending agent; a buffering agent in an amount sufficient to make the composition pH about 4 to about 8; and 300-400 mg/mL glycerin. Exemplary active pharmaceutical ingredients here may be selected from quetiapine, sildenafil, tadalafil, and cinacalcet. Although any suspending agent or agents may be used, in some embodiments, the suspending agent is xanthan gum and HPMC which are present at about 2 to about 6 mg/mL, and about 10 mg/mL, respectively. In some embodiments, the buffering agent is citric acid monohydrate or disodium hydrogen phosphate. Additionally, some embodiments further include microcrystalline cellulose/sodium carboxymethylcellulose, typically at about 20 mg/mL.

Thus, in some embodiments, the suspension comprises an active pharmaceutical ingredient selected from quetiapine, sildenafil, tadalafil, and cinacalcet; about 2 to about 6 mg/mL xanthan gum and about 10 mg/mL HPMC; a buffering agent selected from citric acid monohydrate or disodium hydrogen phosphate; and (optionally) microcrystalline cellulose/sodium carboxymethylcellulose.

For an active pharmaceutical ingredient, having moderate wettability and log P from about 2 to about 2.5, the pharmaceutical composition in the form of a suspension for oral delivery comprises water; a suspending agent; a buffering agent in an amount sufficient to make the composition pH about 3.5 to about 7; and about 100 mg/mL glycerin.

Exemplary active pharmaceutical ingredients include, but are not limited to, ticagrelor, mycophenolate, and aprepitant. In particular embodiments, the suspending agent is xanthan gum which is typically present at about 2 to about 3.5 mg/mL. In some embodiments, the buffering agent is citric acid monohydrate or disodium hydrogen phosphate. Microcrystalline cellulose/sodium carboxymethylcellulose may also be present at about 15 mg/mL.

Thus, some embodiments provide a suspension comprising an active pharmaceutical ingredient selected from ticagrelor, mycophenolate, and aprepitant; xanthan gum at about 2 to about 3.5 mg/mL; citric acid monohydrate or disodium hydrogen phosphate; and optionally microcrystalline cellulose/sodium carboxymethylcellulose.

For an active pharmaceutical ingredient, having good wettability and log P less than about 2, the pharmaceutical composition in the form of a suspension for oral delivery comprises water; a suspending agent; and a buffering agent in an amount sufficient to make the composition pH about 3 to about 6.

In some embodiments, the active pharmaceutical ingredient is selected from zonisamide, and primidone. In some embodiments, the suspending agent is xanthan gum typically at about 3 to about 3.5 mg/mL. In some embodiments, the buffering agent is citric acid monohydrate or disodium hydrogen phosphate. As with other suspensions about 20 mg/mL microcrystalline cellulose/sodium carboxymethylcellulose may be present. Because of the good wettability of the actives in this group, minimal amounts of wetting agent are required. In the case of glycerin up to 25 mg/mL may be used depending on the active. For example, the active zonisamide does not require any glycerin, while primidone formulations use 25 mg/mL.

Thus, some embodiments provide a suspension comprising the active pharmaceutical ingredient selected from zonisamide and primidone; xanthan gum as suspending agent at about 2 to about 3.5 mg/mL; citric acid monohydrate or disodium hydrogen phosphate as the buffering agent; 0 to 25 mg/mL glycerin; and optionally microcrystalline cellulose/sodium carboxymethylcellulose.

Some embodiments employ a stabilizing amount of wetting agent to accommodate a variety of actives. Such pharmaceutical compositions in the form of a suspension for oral delivery comprise an active pharmaceutical ingredient; water; a suspending agent; a stabilizing amount of glycerin; and a buffering agent in an amount sufficient to make the composition pH about 5 to about 7. In some instances, the suspending agent is xanthan gum at about 2 mg/mL. In some instances, the buffering agent is citric acid monohydrate or disodium hydrogen phosphate.

Thus, some embodiments provide a suspension comprising about 2 mg/mL xanthan gum as the suspending agent; citric acid monohydrate or disodium hydrogen phosphate as the buffering agent; and 0 to 25 mg/mL glycerin.

In some embodiments, glycerin is employed as a stabilizer at greater than about 500 mg/mL. Suitable active pharmaceutical ingredients include non-chemotherapeutic active pharmaceutical ingredients. The suspending agent is xanthan gum at about 2 mg/mL and the buffering agent is sufficient to yield a pH of about 5 to about 7.

Other excipients. The suspension may include additional excipients for various purposes such as flavorants, sweeteners, etc.

Non-limiting examples of flavoring agents are synthetic flavor oils and flavoring aromatics and/or natural oils, extracts from plants leaves, flowers, fruits, and so forth and the like or any combinations thereof. These may include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil and the like or any combinations thereof. Also useful as flavors are vanilla, citrus oil, including lemon, orange, grape, lime and grapefruit, and fruit essences, including apple, banana, pear, peach, strawberry, raspberry, cherry, plum, pineapple, apricot, and so forth and the like or any combinations thereof. Solid forms, such as spray dried forms of flavoring agents, may also be useful in the liquid dosage forms disclosed herein.

Several of the materials classified as sweetening agents are sugar alcohols (also known as polyhydric alcohols, polyols and hydrogenated sugars). Several of the commonly used sweetening agents are ionic and have the potential to interact with other components of the suspension. Some sweetening agents are more stable than others in aqueous solution. These will be important factors in the final selection of the sweetening agent. Non-limiting examples of sweetening agents are Glucose, Sucralose, Trehalose, Fructose, Xylose, Dextrose, Galactose, Tagatose, Maltose, Sucrose, Glycerol, Dulcitol, Mannitol, Lactitol, Sorbitol, Xylitol, Saccharine or the corresponding sodium, potassium or calcium salt, Cyclamate or the corresponding sodium or calcium salt, Aspartame, or Acesulfame or the potassium salt thereof, Dulcin or Ammonium glycyrrhizinate, Alitame, Inulin, Isomalt, Neohesperidin dihydrochalcone, Thaumatin and the like or any combinations thereof.

Other known pharmaceutical excipients may be used in the ordinary amounts for their normal purposes, so long as they do not negatively affect the effectiveness or stability of the suspensions. Examples of additional excipients such as but not limited to fillers/vehicles, solvents/co-solvents, preservatives/antioxidants, suspending agents, surfactants, antifoaming agents, buffering agents, chelating agents, sweeteners, flavoring agents, sweetness/flavor enhancing agents, or combinations thereof will be well-known to those of skill in the art.

Methods of treatment. The suspensions disclosed herein are useful with a variety of active pharmaceutical ingredients to treat a variety of conditions, diseases, disorders, or other ailments. In some embodiments, the suspensions are meant to mimic their solid form counterparts, providing the same effectiveness in the same dose. In each case, the method of treating the condition, disease, disorder or other ailment comprises administering the suspension to a patient in need of such treatment to provide a desired or therapeutically acceptable dose of the active pharmaceutical ingredient.

The methods disclosed are for the treatment of a disease or a condition that can be treated by the active pharmaceutical ingredient in the suspension. The method comprises administering to a patient, such as human, an effective dosage amount of a liquid pharmaceutical composition comprising the active pharmaceutical ingredient and one or more pharmaceutically acceptable excipients or additives as disclosed and described herein.

"Effective dosage amount" as used herein with respect to, for example liquid pharmaceutical compositions of the present invention shall mean that dosage that provides the specific pharmacological response for which the active pharmaceutical ingredient administered in a significant number of subjects in need of such treatment. It is emphasized that "effective dosage amount", administered to a particular subject in a particular instance will not always be effective in treating the diseases described herein, even though such dosage is deemed an "effective dosage amount" by those skilled in the art.

The liquid pharmaceutical compositions of the present invention are proposed to have unexpectedly dramatic dissolution profiles. Rapid dissolution of an administered active agent is preferable, as faster dissolution generally leads to greater bioavailability and faster onset of action. To improve the dissolution profile and bioavailability of PDE V inhibitor drug it would be useful to increase dissolution of the PDE V inhibitor drug used so that it could attain a level dose to 100% dissolution of the drug substance.

The liquid pharmaceutical compositions of the present invention comprising the active pharmaceutical ingredient or salt thereof or derivative thereof, exhibit improved or comparable pharmacokinetic profiles as compared to marketed or known compositions of the same active pharmaceutical ingredient or salt or derivative thereof. For example, the Cmax and/or AUC of the liquid pharmaceutical compositions disclosed herein can be greater than or substantially equal to the Cmax and/or AUC for known or marketed compositions, e.g. solid formulations, administered at the same dose. In addition, the Tmax of the liquid compositions of the present invention can be lower than or substantially equal to that obtained for a known or marketed compositions, administered at the same dose. In addition, combinations of an improved or comparable Cmax, AUC and Tmax profile can be exhibited by the liquid compositions of the invention, as compared to known or marketed compositions. In further aspects, the liquid compositions of the present invention may result in minimal different absorption levels when administered under fed as compared to fasting conditions.

The liquid compositions exhibit in comparative pharmacokinetic testing with marketed or known formulations, administered at the same dose, a Tmax not greater than about 90%, not greater than about 80%, not greater than about 70%, not greater than about 60%, not greater than about 50%, not greater than about 30%, not greater than about 25%, not greater than about 20%, not greater than about 15%, not greater than about 10%, or not greater than about 5% of the Tmax exhibited by the marketed or known formulation.

In some embodiments, the liquid compositions exhibit in comparative pharmacokinetic testing with marketed or known formulation, administered at the same dose, a Cmax which is at least about 50%, at least about 100%, at least about 200%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, or at least about 1900% greater than the Cmax exhibited by the marketed or known formulation.

In one of the further aspects, the liquid compositions of the present invention exhibit in comparative pharmacokinetic testing with marketed or known formulation, administered at the same dose, an AUC which is at least about 25%, at least about 50%, at least about 75%, at least about 100%, at least about 125%, at least about 150%, at least about 175%, at least about 200%, at least about 225%, at least about 250%, at least about 275%, at least about 300%, at least about 350%, at least about 400%, at least about 450%, at least about 500%, at least about 550%, at least about 600%, at least about 750%, at least about 700%, at least about 750%, at least about 800%, at least about 850%, at least about 900%, at least about 950%, at least about 1000%, at least about 1050%, at least about 1100%, at least about 1150%, or at least about 1200% greater than the AUC exhibited by the marketed or known formulation.

In some embodiments, the Tmax of the active pharmaceutical ingredient or salt thereof used for the preparation of the liquid composition according to the present invention, when assayed in the plasma of the mammalian subject, is less than about 6 to about 8 hours. In other aspects of the invention, the Tmax of PDE V inhibitor drug or salt thereof is less than about 6 hours, less than about 5 hours, less than about 4 hours, less than about 3 hours, less than about 2 hours, less than about 1 hour, or less than about 30 minutes after administration.

In some aspects, the liquid compositions exhibit improved or comparable bioavailability as compared to known or marketed compositions.

The liquid pharmaceutical compositions of the present invention are suitable for use in the industry.

EXAMPLES

Example 1: Poor Wettability, Log P>2.5

A pharmaceutical composition in the form of a suspension for oral delivery comprises an active pharmaceutical ingredient, having poor wettability and log P>2.5; water; a suspending agent; a buffering agent in an amount sufficient to make the composition pH about 4 to about 8; and 300-400 mg/mL glycerin. Exemplary compounds are described below:

Quetiapine Oral Suspension

| Sr. No. | Ingredients | Role of Ingredients | Tentative Formula % w/v | (mg/mL) |
|---|---|---|---|---|
| 1 | Quetiapine Fumarate Eq to Quetiapine | Active | 0.5 | 5 |
| 2 | Methyl 4-hydroxybenzoate | Preservative | 0.1 | 1 |
| 3 | Propyl 4 hydroxy benzoate | Preservative | 0.01 | 0.1 |
| 4 | Citric monohydrate | Buffering agent | 0.44 | 4.4 |
| 5 | Disodium hydrogen Phosphate dihydrate | Buffering agent | 0.995 | 9.95 |
| 6 | Tween 80 | Wetting agent | 0.125 | 1.25 |
| 7 | 30% Simeticone emulsion | Antifoaming | 0.5 | 5 |
| 8 | Glycerin | Wetting agent | 40 | 400 |
| 9 | Xanthan Gum (Xantural 75) | Viscosity modifier | 0.2 | 2 |
| 10 | Liquid Maltitol (Lycasin 80/55) | Sweetener | 5 | 50 |
| 11 | Sucralose | Sweetener | 0.1 | 1 |
| 12 | Aerosil 200 | Dispersing agent | 0.5 | 5 |
| 13 | Tutti-frutti flavor | Flavor | 0.01 | 0.1 |
| 14 | Water | Vehicle | q.s to 100 ml | q.s to 1 ml |

PDE V Inhibitors

In one of the aspects, general formula of the liquid pharmaceutical compositions according to the present invention may be provided as follows.

| Sr No | Ingredient | Quantity (% w/v) |
|---|---|---|
| 1 | Active pharmaceutical ingredient (PDE V inhibitor drug) | 0.01-25 |
| 2 | | 0.01-10 |
| 3 | Preservative(s) | 0.01-10 |
| 4 | Wetting agent(s) | 0-90 |
| 5 | pH adjusting agent(s)/pH modifying agents | Q.S. to adjust the pH |
| 6 | Buffering agent(s) | Q.S. to adjust the pH |
| 7 | Solvent(s)/co-solvent(s) | Q.S. |
| 8 | Solubilizer(s) | Q.S. |
| 9 | Anti-foaming agent(s) | 0.01-10 |
| 10 | Anti-caking agent(s) | 0-10 |
| 11 | Antioxidant | 0-10 |
| 12 | Surfactant(s) | 0.01-10 |
| 13 | Sweetening agent(s) | 0.01-5 |
| 14 | Flavoring agent(s) | 0.01-5 |
| 15 | Coloring agent(s) | 0-2 |
| 16 | Vehicle(s) | Q.S. |

Q.S. = Quantity Sufficient

Those who are skilled in the art will appreciate that different types of liquid pharmaceutical compositions as described herein can be prepared by using suitable excipients or additives known in the art. Thus, the name of excipients or additives and proportionate range thereof provided in the Table-1 is provided herein for the illustration purpose only and should not be construed as the exact or the only scope of the present invention. The liquid pharmaceutical compositions of the present invention may be prepared using suitable excipients or additives in any suitable amount.

In one of the further aspects, the present invention provides processes for the preparation of the liquid pharmaceutical compositions of PDE V inhibitor drugs.

Below are more specific exemplary formulations using sildenafil and Tadalafil made in accordance with this general description.

Sildenafil Oral Suspension

| Sr. No. | Ingredients | Role of Ingredients | Prototype Formula % w/v | (mg/mL) |
|---|---|---|---|---|
| 1 | Sildenafil | Active | 1 | 10 |
| 2 | sodium benzoate | Preservative | 0.2 | 2 |
| 3 | Glycerin | Wetting agent | 40 | 400 |
| 4 | Sucralose Powder | Sweetener | 0.5 | 5 |
| 5 | 30% Simethicone Emulsion | Antifoaming | 0.05 | 0.5 |
| 6 | Citric acid monohydrate | Buffering agent | 0.28 | 2.8 |
| 7 | Xanthan gum | Viscosity | 0.25 | 2.5 |
| 8 | Tri-sodium citrate dihydrate | Buffering agent | 0.486 | 4.86 |
| 9 | Polysorbate 80 | Wetting agent | 0.1 | 1 |
| 10 | Acesulfame K | Sweetener | 0.1 | 1 |
| 11 | Strawberry Flavor | Flavor | 0.01 | 0.1 |
| 12 | Water | Vehicle | q.s to 100 ml | q.s to 1 ml |

Tadalafil Oral Suspension

| Sr. No. | Ingredients | Role of Ingredients | Prototype Formula % w/v | (mg/mL) |
|---|---|---|---|---|
| 1 | Tadalafil | Active | 0.4 | 4 |
| 2 | sodium benzoate | Preservative | 0.24 | 2.4 |
| 3 | Glycerin | Wetting agent | 40 | 400 |
| 4 | Sucralose Powder | Sweetener | 0.1 | 1 |
| 5 | 30% Simethicone Emulsion | Antifoaming | 0.05 | 0.5 |
| 6 | Citric acid monohydrate | Buffering agent | 0.28 | 2.8 |
| 7 | Xanthan gum | Viscosity | 0.25 | 2.5 |

-continued

| Sr. No. | Ingredients | Role of Ingredients | Prototype Formula % w/v | (mg/mL) |
|---|---|---|---|---|
| 8 | Tri-sodium citrate dihydrate | Buffering agent | 0.486 | 4.86 |
| 9 | Polysorbate 80 | Wetting agent | 0.1 | 1 |
| 10 | Frozen peppermint flavor | Flavour | 0.01 | 0.1 |
| 11 | Water | vehicle | q.s to 100 ml | q.s to 1 ml |

0.1% active may also be used with the remaining excipients are at the same concentration in both strengths

Cinacalcet Oral Suspension

Below is an exemplary suspension having cinacalcet as the active pharmaceutical ingredient.

| Sr No | Name of Ingredient | mg/mL |
|---|---|---|
| 1 | Cinacalcet hydrochloride | 10-40 |
| 2 | Hydroxypropyl methyl cellulose (HPMC) | 0.1-25 |
| 3 | Sucralose | 0.5-5 |
| 4 | Glycerin | Q.S. |
| 5 | Methyl paraben | 0.1-2 |
| 6 | Propyl paraben | 0.1-2 |
| 7 | Simethicone | 0.1-5 |
| 8 | Fraise flavor | 0.05-2 |
| 9 | Polysorbate 80 | 0.01-2 |
| 10 | Triethyl amine | Q.S. to adjust the pH between about 5.0 and 6.5 |
| 11 | Purified water | Q.S. |

Q.S. = Quantity Sufficient

Method of Preparation:

The suspension dosage form of Cinacalcet was prepared according to the process mentioned below.
  (a) Add methyl paraben and propyl paraben in purified water;
  (b) Add sucralose, simethicone, polysorbate 80 and glycerin sequentially;
  (c) Add Cinacalcet or pharmaceutically acceptable salt thereof;
  (d) Add hydroxyprophyl methyl cellulose, triethyl amine (to adjust the pH between about 5.0 and 6.5) and fraise flavor sequentially; and
  (e) Add required quantity of purified water to make up the volume.

A further formulation made with similar techniques as shown in the table below:

| Sr. No. | Ingredients | Role of Ingredients | Prototype Formula % w/v | (mg/mL) |
|---|---|---|---|---|
| 1 | Cinacalcet hydrochloride | Active | 3.6 | 36 |
| 2 | Benecel K4M Pharm CR Hypromellose | Suspending agent | 1 | 10.0 |
| 3 | Sucralose | Sweetener | 0.2 | 2.0 |
| 4 | Glycerin | vehicle | 35 | 350.0 |
| 5 | 30% Simethicone Emulsion | Anti-foaming agent | 0.5 | 5.0 |
| 6 | Strawberry flavor | Flavoring agent | 0.02 | 0.2 |
| 7 | Polysorbate 80 | Wetting agent | 0.025 | 0.25 |
| 8 | Water | Vehicle | q.s to 100 ml | q.s to 1 ml |

*3.6% of cinacalcet HCl may also be used with the remaining excipients' concentrations are same Example 2: Moderate Wettability, Log p about 2 to about 2.5

A pharmaceutical composition in the form of a suspension for oral delivery comprises an active pharmaceutical ingredient, having moderate wettability and log P from about 2 to about 2.5; water; a suspending agent; a buffering agent in an amount sufficient to make the composition pH about 3.5 to about 7; and about 100 mg/mL glycerin. Exemplary compositions are described below:

Ticagrelor Oral Suspension

| Sr. No. | Ingredients | Role of Ingredients | Tentative formula % w/v | Prototype Formula (mg/mL) |
|---|---|---|---|---|
| 1 | Ticagrelor | Active ingredient | 1.20 | 12.00 |
| 2 | Microcrystalline cellulose and Carboxymethylcellulose sodium | Suspending agent | 1.50 | 15.00 |
| 3 | Sodium dihydrogen phosphate dihydrate | Buffering agent | 0.18 | 1.82 |
| 4 | Disodium dihydrogen phosphate dihydrate | Buffering agent | 0.325 | 3.25 |
| 5 | sodium bezoate | Preservative | 0.20 | 2.00 |
| 8 | 30% liquid simethicone | Antifoaming agent | 0.30 | 3.00 |
| 9 | Glycerin | Wetting agent | 10.00 | 100.00 |
| 10 | Polysorbate 80 | Wetting agent | 0.10 | 1.00 |
| 11 | Xanthan gum | Viscosity builder | 0.20 | 2.00 |
| 12 | Sucralose | Sweetener | 0.20 | 2.00 |
| 13 | Raspberry Flavor | Flavoring agent | 0.01 | 0.10 |
| 14 | Purified water | Vehicle | Q.S to 100 ml | Q.s to 1 ml |

Mycophenolate Oral Suspension

| Sr. No. | Ingredients | Role of Ingredients | Prototype Formula % w/v | (mg/mL) |
|---|---|---|---|---|
| 1 | Mycophenolate mofetil | Active | 20 | 200 |
| 2 | Xanthan gum | Suspending agent | 0.2 | 2.0 |
| 3 | Glycerin | Vehicle | 10 | 100.0 |
| 4 | Neosorb 70/70 B (Sorbitol solution) | Vehicle | 10 | 100.0 |
| 5 | 30% Simethicone Emulsion | Anti-foaming agent | 10 | 10.0 |
| 6 | Methyl 4 hydroxy benzoate | Preservatives | 0.252 | 2.52 |
| 7 | Propyl 4 hydroxy benzoate | Preservatives | 0.056 | 0.56 |
| 8 | Polysorbate 80 | Wetting agent | 1 | 10.0 |
| 9 | Sodium diHydrogenPhosphate dihydrate | Buffering agent | 0.0233 | 0.233 |
| 10 | Di sodium hydrogen phosphate dihydrate | Buffering agent | 0.162 | 1.620 |
| 11 | Raspberry Flavor | Flavoring agent | 0.1 | 1.0 |
| 12 | water | Vehicle | q.s to 100 ml | q.s to 1 ml |

The oral pharmaceutical suspension of above composition is prepared by following steps but not limited to:
  A) Take vehicle and add buffering agents and mix till it get dissolved
  B) Add and mix co-solvent until it get dispersed
  C) Add wetting agent and antifoaming agent one by one and mix till it gets dispersed or dissolved
  D) Add API and mix till it gets dispersed
  E) Add suspending agent, preservative, sweetener, flavoring agent, if present, one by one till it dissolved or dispersed
  F) Make volume up to desired batch size Aprepitant Oral Suspension The liquid dosage forms of aprepitant may be made according to the table below:

| Sr. No. | Ingredients | Role of Ingredients | Prototype Formula % w/v | Prototype Formula (mg/mL) |
|---|---|---|---|---|
| 1 | Aprepitant | Active | 2.5 | 25 |
| 2 | Xanthan gum | Suspending agent | 0.3 | 3.0 |
| 3 | Methyl 4 hydroxy benzoate | Preservatives | 0.18 | 1.8 |
| 4 | Ethyl 4 hydroxy benzoate | Preservatives | 0.04 | 0.4 |
| 5 | 30% Simethicone Emulsion | Anti-foaming agent | 0.2 | 2.0 |
| 6 | Poloxamer 188 (Kolliphor P 188) | Wetting agent | 0.1 | 1.0 |
| 7 | Microcrystalline cellulose and Carboxymethylcellulose sodium | Suspending agent | 2 | 20.0 |
| 8 | Sucralose | Sweetener | 0.1 | 1.0 |
| 9 | Tutti Frutti flavour | Flavoring agent | 0.01 | 0.1 |
| 10 | Glycerin | Vehicle | 10 | 100 |
| 11 | Citric Acid monohydrate | buffering agent | 0.0803 | 0.803 |
| 12 | Tri-Sodium Citrate Di-hydrate | buffering agent | 0.3263 | 3.263 |
| 13 | Water | Vehicle | q.s to 100 ml | q.s to 1 ml |

1.6% active may also be used with the remaining excipients' concentration is same The general process for preparing liquid dosage forms of the present invention can be described as follows.
  (a) One or more preservative(s) and one or more buffering agent(s) are solubilized in the suitable vehicle(s)/solvent(s);
  (b) One or more anti-foaming agent(s) and one or more surfactant(s) are dispersed in step (a);
  (c) One or more non-aqueous solution(s) are added in step (b);
  (d) Aprepitant is added in step (c);
  (e) One or more suspending agent(s) are added in step (d);
  (f) One or more sweetening agent(s) and one or more flavoring agent(s) are added in step (e); and
  (g) Making up the volume of step (f) with suitable vehicle(s)/solvent(s).

Example 3: Good Wettability, log P<2

A pharmaceutical composition in the form of a suspension for oral delivery comprises an active pharmaceutical ingredient, having good wettability and log P less than about 2; water; a suspending agent; and a buffering agent in an amount sufficient to make the composition pH about 3 to about 6. Exemplary compositions are discussed below:

Zonisamide Oral Suspension

| Sr. No. | Ingredients | Role of Ingredients | Prototype Formula % w/v | Prototype Formula (mg/mL) |
|---|---|---|---|---|
| 1 | Zonisamide | Active | 2 | 20 |
| 2 | Microcrystalline cellulose and Carboxymethylcellulose sodium | Suspending agent | 2 | 20.00 |
| 3 | Sucralose | Sweetening agent | 0.2 | 2.00 |
| 4 | Xanthan gum | Suspending agent | 0.35 | 3.50 |
| 5 | Sodium Benzoate | Preservatives | 0.1 | 1.00 |
| 6 | Citric Acid monohydrate | Buffering agent | 0.3719 | 3.72 |
| 7 | Tri-Sodium Citrate Di-hydrate | Buffering agent | 0.3592 | 3.59 |
| 8 | Strawberry flavor | Flavoring agent | 0.01 | 0.10 |
| 9 | water | Vehicle | q.s to 100 ml | q.s to 1 ml |

1.0% active may also be used with the remaining excipients' concentration is same Method of Preparation: The process for the preparation of the liquid composition of Zonisamide involves dissolving required quantities of sodium benzoate, citric acid monohydrate, tri-sodium citrate and sucralose in purified water, followed by dispersing required quantities of Microcrystalline Cellulose & Carboxymethylcellulose Sodium Dispersion, xanthan gum, Zonisamide and Strawberry flavor separately in purified water, mixing both the mixtures, homogenizing it and making up the final volume to the required quantity of batch size with purified water.

Primidone Oral Suspension

| Sr. No. | Ingredients | Role of Ingredients | Prototype Formula % w/v | Prototype Formula (mg/mL) |
|---|---|---|---|---|
| 1 | Primidone | Active | 5 | 50 |
| 2 | Methyl 4-hydroxybenzoate | Preservative | 0.18 | 1.8 |
| 3 | Ethyl 4-hydroxybenzoate | Preservative | 0.06 | 0.6 |
| 4 | Citric monohydrate | Buffering agent | 0.0803 | 0.803 |
| 5 | Tri sodium citrate dihydrate | Buffering agent | 0.3263 | 3.263 |
| 6 | Polysorbate 80 | Wetting agent | 0.05 | 0.5 |
| 7 | 30% Simeticone emulsion | Antifoaming | 0.2 | 2 |
| 8 | Glycerin | Wetting agent | 2.5 | 25 |
| 9 | Xanthan Gum | Viscosity modifier | 0.3 | 3 |
| 10 | Liquid Maltitol | Sweetener | 2.5 | 25 |
| 11 | Sucralose | Sweetener | 0.1 | 1 |
| 12 | Propylene Glycol | Wetting agent | 2 | 20 |
| 13 | Artificial Raspberry Flavor | Flavor | 0.01 | 0.1 |
| 14 | Water | Vehicle | q.s to 100 ml | q.s to 1 ml |

Example 4: Stability Testing

Stability testing was performed on each of the suspensions as outlined in the tables below. In each instance, the suspension was found to be stable.

Quetiapine

| Test parameters | INITIAL | 25/40 3 M | 25/40 6 M | 2-8 3 M | 2-8 6 M |
|---|---|---|---|---|---|
| Description | Off white suspension | Off white suspension | Off white suspension | Off white suspension | Off white suspension |
| Assay of quetiapine | 98.4 | 101 | 99.60% | 99.1 | 98.80% |
| Assay of Methyl Paraben | 101.1 | 98.4 | 98.40% | 100.9 | 98.20% |
| Assay of Propyl Paraben | 99.8 | 98.7 | 98.80% | 100.7 | 97.20% |
| pH | 5.67 | 5.56 | 5.62 | 5.57 | 5.64 |
| Related Substances % | | | | | |
| IMP G | 0.08 | 0.21 | 0.31% | 0.1 | 0.10% |
| Unknown impurity | 0.03 | 0.07 | 0.13% | 0.04 | 0.04% |
| Total impurities | 0.23 | 0.49 | 0.61% | 0.25 | 0.24% |

Sildenafil

| Test parameters | Specification (shelf life) | INITIAL | 40/75 3 M | 40/75 6 M | 25/60 3 M | 25/60 6 M |
|---|---|---|---|---|---|---|
| Description | White to off white suspension | White to off white suspension | White to off white suspension | White to off white suspension | White to off white suspension | White to off white suspension |
| Assay of Sildenafil citrate | 95-105% | 99.40% | 100 | 102.80% | 98.6 | 98.90% |
| Assay of Sodium Benzoate | 80-110% | 98.10% | 97.6 | 100.00% | 98.4 | 98.90% |
| pH | 3.5-5.5 | 4.66 | 4.76 | 4.62 | 4.74 | 4.6 |
| Related Substances | | | | | | |
| Sildenafil Isobutyl analogue [Ph. Eur. Impurity A] | Not more than 0.5% | ND | ND | | ND | |
| Sildenafil N-oxide [Ph. Eur. Impurity-B] | Not more than 0.30% | 0.02 | 0.03% | 0.01% | 0.04% | 0.01% |
| Single maximum unknown impurity | Not more than 0.2% | 0.02 | 0.03 | 0.02% | 0.04 | 0.02% |
| Total impurities | Not more than 1.0% | 0.00 | 0.06 | 0.07% | 0.07 | 0.06% |

Tadalafil

| Test parameters | INITIAL | 40° C./ 25% 6 M | 25° C./ 60% 6 M |
|---|---|---|---|
| Description | Off white suspension | Off white suspension | Off white suspension |
| Assay of Tadalafil | 101.7% | 102.3% | 101.0% |
| Assay of Sodium Benzoate | 99.60% | 102.3% | 101.3% |
| pH | 4.83 | 5.0 | 5 |
| Impurity A/L-Tadalafil of Trance impurity | NP | NP | NP |
| Related substances by HPLC | | | |
| Unspecified Impurities | ND | 0.01 | ND |
| Total impurities | ND | 0.02 | ND |

Cinacalcet

The liquid dosage from prepared according to the examples above were evaluated for their storage stability under different storage conditions. It was surprisingly found that the liquid dosage form of Cinacalcet is stable for prolonged time when tested under different storage conditions. The results of the stability studies conducted are summarized in the table below. These results also show that because of their prolonged storage stability, the liquid dosage forms of the present invention can become a useful alternative to the marketed drug (Sensipar®).

| Test Parameters | Specification | Results | | | | | | |
|---|---|---|---|---|---|---|---|---|
| | | Initial | 40° ± 2° C./25 ± 5 RH | | | | 25° ± 2° C./40 ± 5 RH | |
| | | | 1 M | 2 M | 3 M | 6 M | 3 M | 6 M |
| Description | White to brownish white suspension | Complies | Complies | Complies | Complies | Complies | Complies | Complies |
| Assay of Cinacalcet HCl | 95-105% | 100.0% | 102.0% | 103.4% | 103.8% | 101.3% | 104.2% | 98.8% |
| Assay of methyl paraben | 90-110% | 100.6% | 102.4% | 101.3% | 102.3% | 100.2% | 103.4% | 100.0% |
| Assay of propyl paraben | 90-110% | 96.1% | 97.0% | 97.6% | 98.4% | 94.5% | 100.0% | 94.7% |
| pH | Between about 5.5 and 6.5 | 5.54 | 5.56 | 5.53 | 5.47 | 5.74 | 5.48 | 5.74 |
| Related Substances | | | | | | | | |
| Amine impurity | NMT 0.2% | ND | 0.01% | 0.01% | 0.06% | ND | 0.02% | 0.01% |
| Alcohol impurity | NMT 0.2% | ND | ND | ND | ND | ND | ND | ND |
| Mesylated impurity | NMT 0.2% | ND | ND | ND | ND | ND | ND | ND |
| Regio impurity | NMT 0.2% | ND | ND | ND | ND | 0.02% | ND | ND |
| Dimer Impurity | NMT 0.2% | 0.03% | 0.02% | 0.03% | ND | 0.01% | ND | ND |
| Single maximum impurity | NMT 0.2% | 0.04% | 0.06% | 0.06% | 0.10% | 0.21% | 0.05% | 0.06% |
| Total impurities | NMT 2.0% | 0.15% | 0.23% | 0.23% | 0.38% | 0.23% | 0.14% | 0.14% |
| Viscosity | To be recorded | 243.75 | 244.50 | 229.00 | 239.50 | 232.00 | 231.50 | 236.6 |

| | | Initial | 40/25-6 M | 25/40-6 M |
|---|---|---|---|---|
| 1 | Description | White to offwhite suspension | White to offwhite suspension | White to offwhite suspension |
| 2 | Assay of Cinacalcet HCL | 98.00 | 99.8 | 96.7 |
| 3 | Assay of Methyl Paraben | 100.00% | 98.2 | 104.7 |
| 4 | Assay of Propyl paraben | 103.30 | 93.6 | 100.2 |
| 5 | pH of Suspension | 5.79 | 5.86 | 5.85 |
| 6 | Related substances (By HPLC) | | | |
| | Amine impurity | 0.04% | 0.07 | 0.01 |
| | Alcohol impurity | ND | ND | ND |
| | Mesylated impurity | ND | ND | ND |
| | Regio impurity | ND | ND | ND |
| | Dimer impurity | 0.01% | ND | ND |
| | Any individual unspecified impurity | 0.07(RRT 0.93) | 0.18(RRT 0.46) | 0.04(RRT 0.46) |
| | Total Impurities | 0.21% | 0.54 | 0.12% |

Mycophenolate

| Sr. No | Test parameters | FTFMYCL 0046 Initial | FTFMYCL 0074 40/25-3 M | FTFMYCL 0075 25/40-3 M | FTFMYCLS 0050 25/40-6 M |
|---|---|---|---|---|---|
| 1 | Description | White to offwhite suspension | White to offwhite suspension | White to offwhite suspension | White to offwhite suspension |

-continued

| Sr. No | Test parameters | FTFMYCL 0046 Initial | FTFMYCL 0074 40/25-3 M | FTFMYCL 0075 25/40-3 M | FTFMYCLS 0050 25/40-6 M |
|---|---|---|---|---|---|
| 2 | pH | 7.2 | 6.42 | 6.42 | 6.55 |
| 3 | Assay of mycophenolate Mofetil | 101.30% | 90.00% | 96.50% | 100.00% |
| 4 | Assay of methyl paraben | 103.40% | 89.50% | 94.00% | 94.40% |
| 5 | Assay of propyl paraben | 109.20% | 94.00% | 94.00% | 94.40% |
| 6 | Related Substances | | | | |
|   | Mycophenolic acid (NMT 3.3%) | 0.09% | 5.51% | 0.71% | 1.35% |
|   | N oxide analog | ND | ND | ND | ND |
|   | Unknown impurity @ RRT-0.37 | ND | 0.36 | 0.06% | 0.12% |
|   | Total impurities | 0.09% | 6.04% | 0.81% | 1.47% |

Example 5: Stability Studies of the Liquid Dosage Forms of Aprepitant

The liquid dosage forms of the present invention were evaluated for their storage stability under different storage conditions. It was surprisingly found that the ready to use, oral suspension dosage forms of Aprepitant prepared according to the present invention found stable for prolonged time when tested under different storage conditions. The results of the stability studies conducted are summarized in the table below. These results also show that because of their prolonged storage stability, the liquid dosage forms of the present invention can become a useful alternative to the marketed EMEND® powder for oral suspension.

| S. No | Test parameters | Initial | 40/25-3 M | 25/40-3 M |
|---|---|---|---|---|
| 1 | Description | White to off-white suspension | White to off-white suspension | White to off-white suspension |
| 2 | pH | 5.52 | 5.52 | 5.52 |
| 3 | Assay of Aprepitant | 97.50% | 98.1 | 99.9 |
| 4 | Assay of methylparaben | 96.90% | 98.5 | 98.7 |
| 5 | Assay of ethylparaben | 95.30% | 97 | 97 |
| 6 | Related Substances | | | |

-continued

| S. No | Test parameters | Initial | 40/25-3 M | 25/40-3 M |
|---|---|---|---|---|
|   | Impurity A | ND | ND | ND |
|   | Impurity B | ND | ND | ND |
|   | Impurity C | 0.03 | 0.03 | 0.03 |
|   | Single maximum impurity | BQL | ND | ND |
|   | Total impurities | 0.05% | 0.03 | 0.03 |
| 7 | Stereochemical purity | 100% | 100% | 100% |
|   | Stereoisomer at RRT about 0.60 | ND | ND | ND |
|   | Stereoisomer at RRT about 0.80 | ND | ND | ND |
|   | Any other individual stereoisomer | ND | ND | ND |
|   | Total Stereoisomeric impurities | ND | ND | ND |

Zonisamide

The oral liquid pharmaceutical composition prepared according to Example 1 exhibits an unexpected stability profile when tested after one (1), three (3) and (6) months under the conditions 40° C./25% RH and 25° C./40% RH. The liquid composition according to the present invention possess very less amount of impurities and highest degree of purity. The results of the stability tests conducted are summarized in the table below.

|   |   | Initial | 40/25-3 M | 25/40-3 M | 40/25-6 M | 25/40-6 M |
|---|---|---|---|---|---|---|
| 1 | Description | White to off white suspension | White to off white suspension | White to off white suspension | White to off white suspension | White to off white suspension |
| 2 | PH | 4.5 | 4.2 | 4.3 | 4.4 | 4.4 |
| 3 | Assay of zonisamide | 100.9 | 101.90% | 100.50% | 102.40% | 101.70% |
|   | Assay of sodium benzoate | 89.8 | 100.90% | 94.60% | 101.40% | 99.80% |
| 4 | Impurity A | ND | ND | ND | ND | 0.01 |
|   | Single max impurity | 0.05 | 0.06 | 0.06 | 0.05 | 0.05 |
|   | Total impurities | 0.05 | 0.06 | 0.07 | 0.05 | 0.05 |

Primidone

| Test parameters | INITIAL | 25/40 6 M | 40/25 6 M |
|---|---|---|---|
| Description | White to off white suspension | White to off white suspension | White to off white suspension |
| Assay of primidone | 103.9 | 103.2 | 102.7 |
| Assay of Methyl Paraben | 99.3 | 101.6 | 99.3 |
| Assay of ethyl Paraben | 98.8 | 101.8 | 99.4 |
| pH | 5.55 | 5.5 | 5.55 |
| Related Substances % | | | |
| IMP A | ND | ND | ND |
| IMP B | ND | ND | ND |
| IMP C | ND | ND | ND |
| IMP D | ND | ND | ND |
| IMP E | ND | ND | ND |
| IMP F | 0.13 | 0.11 | 0.11 |
| Unknown impurity | 0.04 | 0.04 | 0.04 |
| Total impurities | 0.17 | 0.15 | 0.15 |

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Although the present invention has been described in considerable detail with reference to certain preferred embodiments thereof, other versions are possible. Therefore, the spirit and scope of the appended claims should not be limited to the description and the preferred versions contained within this specification.

What is claimed is:
1. A pharmaceutical oral suspension, comprising:
mycophenolate mofetil in an amount of about 200 mg/ml;
a mycophenolate glycerol ester;
one or more pharmaceutically acceptable excipients; and
a vehicle comprising water.

* * * * *